US009933373B2

(12) United States Patent
Vild et al.

(10) Patent No.: US 9,933,373 B2
(45) Date of Patent: Apr. 3, 2018

(54) GLASS SHEET ACQUISITION AND POSITIONING MECHANISM FOR AN INLINE SYSTEM FOR MEASURING THE OPTICAL CHARACTERISTICS OF A GLASS SHEET

(71) Applicant: GLASSTECH, INC., Perrysburg, OH (US)

(72) Inventors: Michael J. Vild, Toledo, OH (US); Stephen D. Snyder, Jr., Whitehouse, OH (US)

(73) Assignee: GLASSTECH, INC., Perrysburg, OH (US)

( * ) Notice: Subject to any disclaimer, the term of this patent is extended or adjusted under 35 U.S.C. 154(b) by 606 days.

(21) Appl. No.: 14/264,231

(22) Filed: Apr. 29, 2014

(65) Prior Publication Data

US 2015/0308943 A1    Oct. 29, 2015

(51) Int. Cl.
  *G01N 21/13*   (2006.01)
  *G01N 21/958*   (2006.01)
  *G01N 21/896*   (2006.01)

(52) U.S. Cl.
  CPC ......... *G01N 21/958* (2013.01); *G01N 21/896* (2013.01); *G01N 2021/9586* (2013.01); *G01N 2201/0635* (2013.01)

(58) Field of Classification Search
  CPC ......... G01N 2021/9586; G01N 21/896; G01N 21/958; G01N 2201/0635
  USPC ............................. 356/239.1, 244; 348/125
  See application file for complete search history.

(56) References Cited

U.S. PATENT DOCUMENTS

| 4,325,723 | A |   | 4/1982 | Keller et al. |
| 4,895,244 | A |   | 1/1990 | Flaugher et al. |
| 5,238,100 | A |   | 8/1993 | Rose, Jr. et al. |
| 5,691,811 | A |   | 11/1997 | Kihira |
| 5,870,204 | A | * | 2/1999 | Chiu .................. G01N 21/8903 356/430 |

(Continued)

OTHER PUBLICATIONS

Adamo et al, Calibration of an inspection system for online quality control of satin glass (Year: 2010).*

(Continued)

*Primary Examiner* — Shan E Elahi
(74) *Attorney, Agent, or Firm* — Brooks Kushman P.C.

(57) ABSTRACT

A glass sheet acquisition and positioning mechanism and associated method are utilized in an in-line glass sheet optical inspection system. The mechanism includes an exterior support frame mounted in proximity to one of the glass sheet processing system conveyors, and an interior support frame operably connected to the exterior support frame such that the interior support frame may be selectively positioned from its first orientation to a second orientation whereby the retained glass sheet is positioned between the camera and the screen at a preselected position. The interior support frame is also operably connected to the exterior support frame to provide for positioning of the interior support frame to a third orientation in which the glass sheet is released from the interior support frame for continued movement on the conveyor. An in-line glass sheet optical inspection system incorporating the glass sheet acquisition and positioning mechanism is also disclosed.

26 Claims, 6 Drawing Sheets

(56) References Cited

U.S. PATENT DOCUMENTS

| | | | | |
|---|---|---|---|---|
| 5,887,077 A * | 3/1999 | Bongardt | ................... | G01J 3/50 |
| | | | | 382/149 |
| 6,208,412 B1 | 3/2001 | Ladewski | | |
| 6,359,686 B1 * | 3/2002 | Ariglio | .............. | G01N 21/8901 |
| | | | | 356/239.1 |
| 6,724,477 B2 * | 4/2004 | Kitamura | ........... | G01N 21/8803 |
| | | | | 356/237.1 |
| 7,403,872 B1 * | 7/2008 | St. Onge | ................... | B07C 5/08 |
| | | | | 324/237 |
| 3,049,879 A1 | 11/2011 | Shetterly et al. | | |
| 8,049,879 B2 * | 11/2011 | Shetterly | .............. | G01N 21/958 |
| | | | | 356/239.2 |
| 8,256,244 B2 * | 9/2012 | Imaichi | ................. | C03B 23/023 |
| | | | | 65/106 |
| 2002/0063862 A1 * | 5/2002 | Kitamura | ........... | G01N 21/8803 |
| | | | | 356/239.2 |
| 2002/0123868 A1 * | 9/2002 | Yajima | .................... | G06T 15/20 |
| | | | | 703/2 |
| 2004/0057046 A1 * | 3/2004 | Abbott | ................. | G01N 21/896 |
| | | | | 356/239.1 |
| 2008/0032066 A1 * | 2/2008 | Stiblert | ............... | G03F 7/70391 |
| | | | | 427/595 |
| 2008/0256704 A1 * | 10/2008 | Conway | ............... | A47C 19/045 |
| | | | | 5/412 |
| 2009/0199594 A1 * | 8/2009 | Abbott | ................ | C03B 27/0417 |
| | | | | 65/29.14 |
| 2009/0282871 A1 | 11/2009 | Shetterly et al. | | |
| 2010/0028567 A1 * | 2/2010 | Suizu | ................... | G01M 11/081 |
| | | | | 428/1.32 |
| 2010/0218555 A1 * | 9/2010 | Tomioka | ............. | C03B 23/0254 |
| | | | | 65/29.1 |
| 2012/0098959 A1 * | 4/2012 | Addington | ........... | G01N 21/958 |
| | | | | 348/125 |
| 2012/0234459 A1 * | 9/2012 | Nally | ................ | B32B 17/10807 |
| | | | | 156/64 |
| 2013/0091896 A1 * | 4/2013 | Nitschke | ................. | C03B 23/03 |
| | | | | 65/106 |
| 2014/0146165 A1 * | 5/2014 | Furnas | ................. | G01N 21/896 |
| | | | | 348/92 |
| 2014/0240489 A1 * | 8/2014 | Furnas | ................. | G01N 21/896 |
| | | | | 348/131 |
| 2016/0257598 A1 * | 9/2016 | Vild | ..................... | B65G 47/902 |

OTHER PUBLICATIONS

International Search Report and Written Opinion of PCT/US2015/018229, dated May 20, 2015, 8 pages.

U.S. Patent Application "Glass Sheet Acquistion and Positioning System and Associated Method for an Inline System for Measuring the Optical Characteristics of a Glass Sheet", U.S. Appl. No. 14/639,655, 26 Pages.

U.S. Office Action Dated Feb. 3, 2017, U.S. Appl. No. 14/639,655, 21 Pages.

U.S. Final Office Action Dated Oct. 18, 2017, U.S. Appl. No. 14/639,655, 17 Pages.

Notification of Transmittal of the International Search Report and Written Opinion of the International Searching Authority, or the Declaration, Dated Apr. 7, 2016, Application No. PCT/US16/16095, Applicant Glasstech, Inc., 12 Pages.

* cited by examiner

GLASS SHEET ACQUISITION AND POSITIONING MECHANISM FOR AN INLINE SYSTEM FOR MEASURING THE OPTICAL CHARACTERISTICS OF A GLASS SHEET

TECHNICAL FIELD

This invention relates to a method and apparatus for measuring transmitted optical distortion in glass sheets installed in-line in a glass sheet processing system.

BACKGROUND

Manufacturers of glass sheets, particularly glass sheets formed into various curved shapes for use as automotive windshields, backlites, and sidelites, are interested in measuring and evaluating the amount of optical distortion in the formed sheets that might be perceived by a human observer, such as the operator or passenger in a vehicle in which the glass may be mounted as the windshield, backlite, or sidelite. Manufacturers, as well, desire to identify small marks or other defects that are visible on the surface of the form glass sheets.

Various types of glass sheet optical inspection systems are known. One known optical inspection system is disclosed in United States Application Publication No. 2012/0098959 A1, which application is also assigned to the assignee of the invention disclosed herein. This disclosed optical inspection system may be implemented in either a laboratory (i.e., off-line) or an in-line configuration in which the inspection system is mounted to inspect glass sheets as they are being conveyed in a processing system. Thus, it may be desirous to implement an in-line configuration which includes a simple, reliable mechanism for collecting a glass sheet as it is conveyed during processing, positioning the glass sheet for image acquisition by the inspection system, and returning the glass sheet to the conveyor.

SUMMARY

The disclosed glass sheet acquisition and positioning mechanism and associated method are utilized in an in-line optical inspection system for measuring the optical characteristics of a glass sheet, wherein the in-line system is installed in a system for fabricating glass sheets, which system includes one or more processing stations and one or more conveyors for conveying the glass sheet from station to station during processing. In addition to the disclosed glass sheet acquisition and positioning mechanism, the optical inspection system includes a background screen having a predefined contrasting pattern, a digital camera for acquiring an image of the background screen with a glass sheet positioned between the camera and the screen at a preselected position, and a computer including logic for receiving the captured image data and performing one or more optical processing operations to analyze the optical characteristics of the glass sheet.

The glass sheet acquisition and positioning mechanism includes an exterior support frame mounted in proximity to one of the conveyors at a desired location, and an interior support frame including one or more locators connected to the frame such that, when the interior support frame is positioned in a first, generally horizontal orientation in the path of the glass sheet as it is conveyed on the conveyor, the locators are positioned to catch and retain a glass sheet as it is moving on the conveyor. The interior support frame is operably connected to the exterior support frame such that the interior support frame may be selectively positioned from its first orientation to a second, upwardly tilted orientation whereby the upstream end of the interior support frame is elevated from the plane of the conveyor with the retained glass sheet positioned between the camera and the screen at a preselected position. The interior support frame is also operably connected to the exterior support frame to provide for positioning of the interior support frame to a third, upwardly tilted orientation in which the downstream end of the interior support frame is upwardly tilted from the plane of the conveyor, thereby releasing the glass sheet retained in the interior support frame for continued movement on the conveyor.

An in-line glass sheet optical inspection system and method are also disclosed. The in-line glass sheet optical inspection system is mounted to inspect glass sheets as they are transported on a conveyor associated with a glass sheet processing system which performs one or more heating, bending, tempering, heat-strengthening, or other fabricating operations on the glass sheets. The disclosed optical inspection system includes a background screen including contrasting elements arranged in a pre-defined pattern, a digital camera for acquiring an image of the background screen, and a glass sheet acquisition and positioning mechanism for receiving a glass sheet at it is conveyed on one of the glass sheet processing system conveyors, momentarily removing the glass sheet from the conveyor and positioning the glass sheet in the path between the camera and the background screen so that the camera may capture an image of the pattern transmitted through the glass sheet, and then re-positioning the glass sheet on the conveyor. The disclosed in-line optical inspection system also includes a computer including logic for receiving the captured image data and performing one or more optical processing operations to analyze the optical characteristics of the glass sheet and display or otherwise report selected information associated with the analysis.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
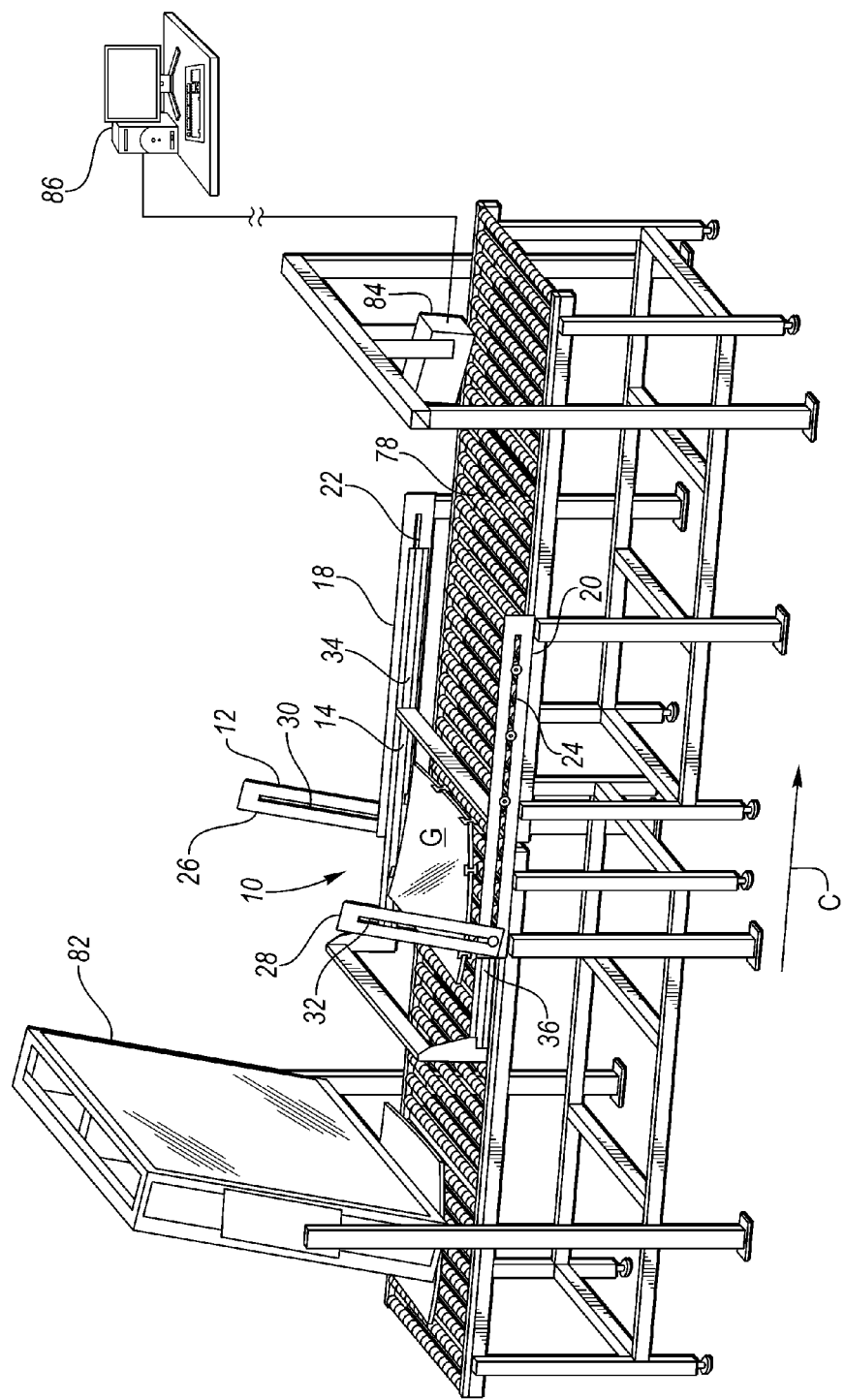
FIG. 1 is a perspective view of one embodiment of the disclosed glass sheet optical inspection system.

Referring to FIG. 1, a glass sheet acquisition and positioning mechanism 10 is disclosed for utilization in an in-line optical inspection system, wherein the optical inspection system is installed in a glass sheet fabricating system that includes one or more processing stations and one or more conveyors 78 for conveying glass sheets from station to station during processing. The optical inspection system also includes a background screen 82 having a predefined pattern, a digital camera 84 for acquiring an image of the background screen with a glass sheet positioned between the camera and the screen at a preselected position, and a computer 86 including logic for receiving the captured image data and performing one or more processing operations to analyze the optical characteristics of the glass sheet.

The glass sheet acquisition and positioning mechanism 10 includes an exterior support frame 12 mounted in proximity to one of the conveyors at a desired location, and an interior support frame 14 that is supported by and is movable with respect to the exterior support frame to a series of preselected positions to catch and retain a glass sheet as it is conveyed on the conveyor, position the glass sheet in the desired orientation for image acquisition by the inspection system, and thereafter deposit the glass sheet on the conveyor. The interior support frame 14 includes one or more locators 16 (best shown in FIG. 4) which are mounted on the support frame in positions suitable to engage a glass sheet as it is moving on the conveyor and retain the sheet for repositioning as described above.

Figure 2:
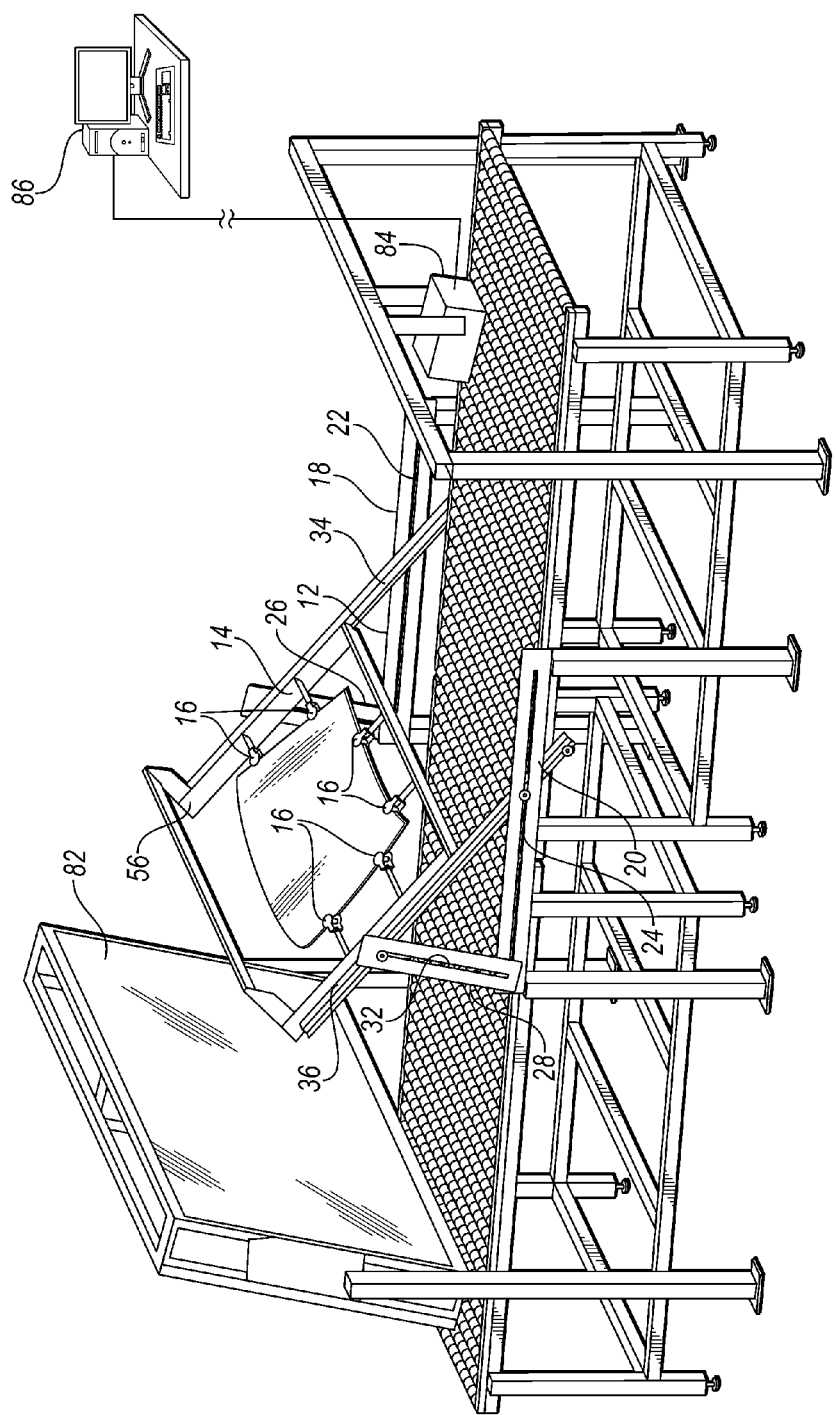
FIG. 2 is a perspective view of the disclosed glass sheet optical inspection system of FIG. 1 with the glass sheet acquisition and positioning mechanism positioned to present the glass sheet for image acquisition.

Referring now to both FIGS. 1 and 2, as shown in the disclosed embodiment, the exterior support frame 12 of mechanism 10 may include first and second generally horizontal rails 18, 20 which are mounted, respectively, on opposite sides of the conveyor. Each of the horizontal rails 18, 20 has a guideway 22, 24, which, in the disclosed embodiment, are formed as horizontally oriented slots (i.e., parallel to the direction of glass sheet conveyance). The exterior support frame 12 may also include first and second generally vertical rails 26, 28, also mounted, respectively, on opposite sides of the conveyor. Vertical rails 26, 28 may each also include a guideway 30, 32, which, again, may be implemented in the form of a generally vertically oriented slot.

Figure 4:
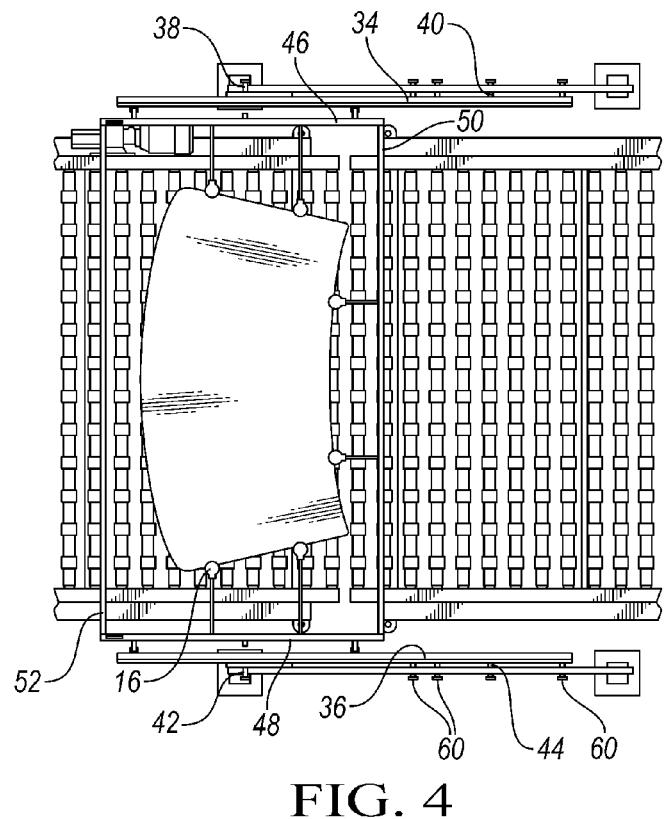
FIG. 4 is a top view of one embodiment of the glass sheet acquisition and positioning mechanism.
Figure 5:
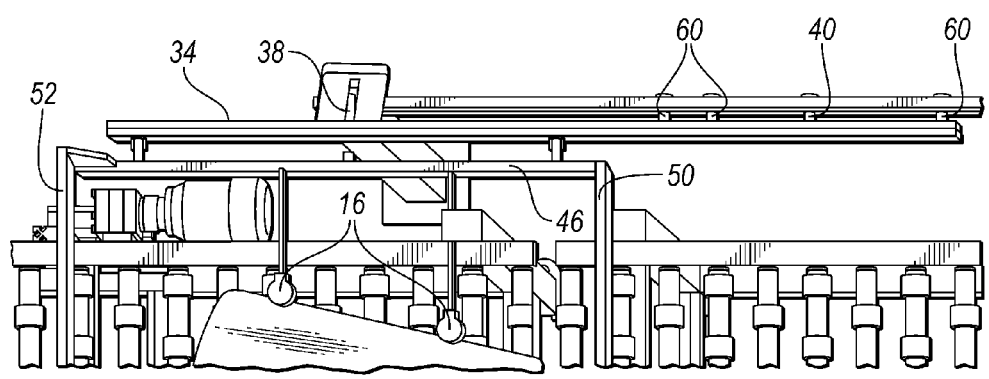
FIG. 5 is a partial top view of the glass sheet acquisition and positioning mechanism of FIG. 4.
Figure 6:
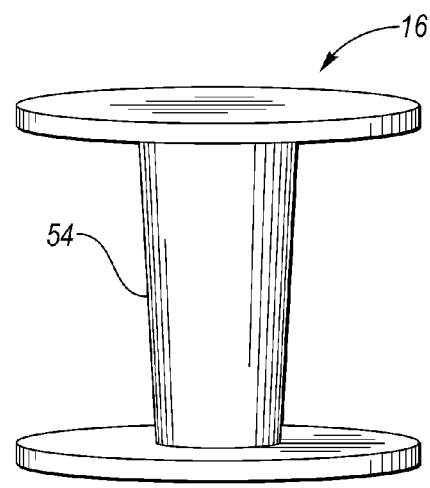
FIG. 6 is a side view of one embodiment of a locator which may be utilized in the glass sheet acquisition and positioning mechanism.
Figure 7:
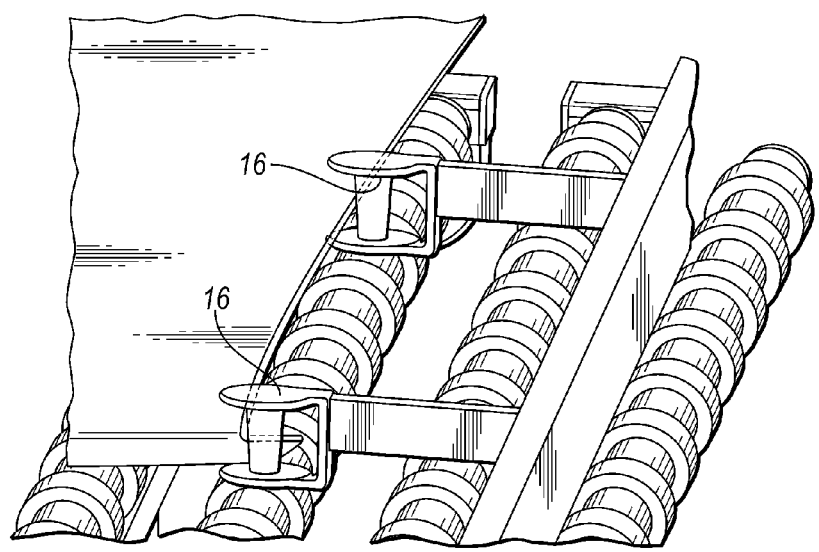
FIG. 7 is a partial perspective view of the interior support frame of the glass sheet acquisition and positioning mechanism of FIG. 4 with a glass sheet engaged by two locators.

As is best shown in FIGS. 4 and 5, first and second support arms 34, 36 are operably connected to the exterior support frame 12 for slidable and pivotal movement with respect to the frame 12. The first support arm 34 may include a first positioning guide 38 secured to the support arm 34 and engaging guideway 30 of the first generally vertical rail 26, and a second positioning guide 40, also secured to the support arm 34 and engaging guideway 22 of the first generally horizontal rail 18. In the disclosed embodiment, guide 40 is a cylindrically shaped pin of sufficient length and diameter to fit securely and slide smoothly within guideway 30. Similarly, the second support arm 36 may include a first positioning guide 42 secured to the support arm 36 and engaging guideway 32 of the second generally vertical rail 28, and a second positioning guide 44, also secured to the support arm 36 and engaging guideway 24 of the second generally horizontal rail 20. Again, guide 42 is implemented in the disclosed embodiment as a cylindrically shaped pin.

Referring again to FIGS. 4 and 5, the interior support frame 14 of the mechanism 10 may include first and second spaced-apart and generally parallel side members 46, 48, and a cross-member 50 extending transverse to, and interconnecting, the side members 46, 48, thereby defining a generally U-shaped frame. The interior support frame 14 may be releasably supported on the first and second support arms 34, 36 as described hereinafter and oriented such that the open end of the interior support frame 14 is facing the upstream direction of conveyance when the interior support frame is positioned in a generally horizontal orientation in the plane of the glass sheets on the conveyor.

The interior support frame 14 may also include one or more additional cross-members to increase the rigidity of the support frame 14, such as second cross-member 52. Any such additional cross-members (such as cross-member 52) interconnect side members 46-48, but are spaced above the plane of conveyance of the glass sheet, such that they do not block the path of the moving glass sheet when the interior support frame 14 is positioned to catch and engage a glass sheet on the conveyor.

As is best illustrated in FIGS. 4-7, the interior support frame 14 may also include one or more locators 16 mounted in position to engage a glass sheet as it is conveyed on the conveyor and retain the sheet for further positioning to accomplish the in-line optical inspection. In the illustrated embodiment, locators 16 are mounted on either the side members 46, 48 or cross-member 50. One or more of the locators may movable from non-engagement positions to positions in which the locators engage the glass sheet edge and secure the sheet on the contacting surfaces 54 of each of the locators, such that the sheet can be lifted from the conveyor and positioned as desired. In one embodiment, each of the locators which are positioned along the side edge of the glass sheet include conventional actuators (not shown) which may be activated to move the locators inwardly towards and into contact with the glass sheet immediately after the sheet contacts the locators positioned at the downstream end of the conveyor to secure the sheet on the interior support frame 14, and thereafter activated to move the locators outwardly and away from contact with the glass sheet to allow the sheet to disengage from the support frame 14 and move on the conveyor 78.

In another contemplated embodiment, one or more of the locators 16 may be mounted for movement from a position out of the plane of the conveyor (such as below and between the conveyor rolls on a roller conveyor) to a position in the plane of conveyance to contact, position, to assist in positioning the glass sheet on the conveyor prior to securing the sheet within the interior support frame 14. These locators may include conventional sensors and actuators to sense the presence and location of a glass sheet on the conveyor and move into contact with the sheet as desired. One type of such a positioning system which may be adaptable to assist in positioning and securing the glass sheet on the interior frame 14 is disclosed in U.S. Patent Application Publication No. 2013/0091896 A1 (see, in particular, positioning apparatus 54 and positioners 55, FIGS. 4 and 6-10, p. 4, ¶¶ 39, 41), the relevant portions of which Publication are hereby incorporated herein in their entirety. In this alternative embodiment, one or more locators 16 may also be mounted on the interior support frame 14. Alternatively, or additionally, other conventional gripping devices, such as suction cups or other mechanical grippers, may be mounted on support frame 14 to secure the glass sheet to the support frame 14 once the sheet has been retained in proper position by the locators 16 for acquisition by the support frame 14.

The contacting surface 54 of the locator may be suitably shaped to allow the glass sheet to slide under its own weight along the contacting surface and properly orient the glass sheet as it engages the locators 16 on the perimeter edge of the glass sheet. In the disclosed embodiment (best shown in FIGS. 6 and 7), the contacting surface 54 of the locators 16 is shaped as a truncated frusto-conical surface. It will, however, be appreciated by those skilled in the art that various surface configurations may be adopted for contacting surface 54 to effectively retain and achieve the desired orientation of the glass sheet as it is retained within the locators 16 and repositioned for imaging.

One or more conventional sensors (not shown) may be mounted on one or more of the locators 16 and operably connected to a controller, such as computer 86. The controller may also be operably connected to one or more conventional actuators (not shown) and suitably programmed to receive signals from the one or more sensors and determine from those signals when a glass sheet has contacted the sensors, then transmit signals to the actuators to position the mechanism 10 as hereinafter described to present the retained glass sheet in the appropriate position to acquire an image of the sheet and thereafter lower the glass sheet onto the conveyor and release the glass sheet from the mechanism 10 for conveyance for further processing.

Figure 3:
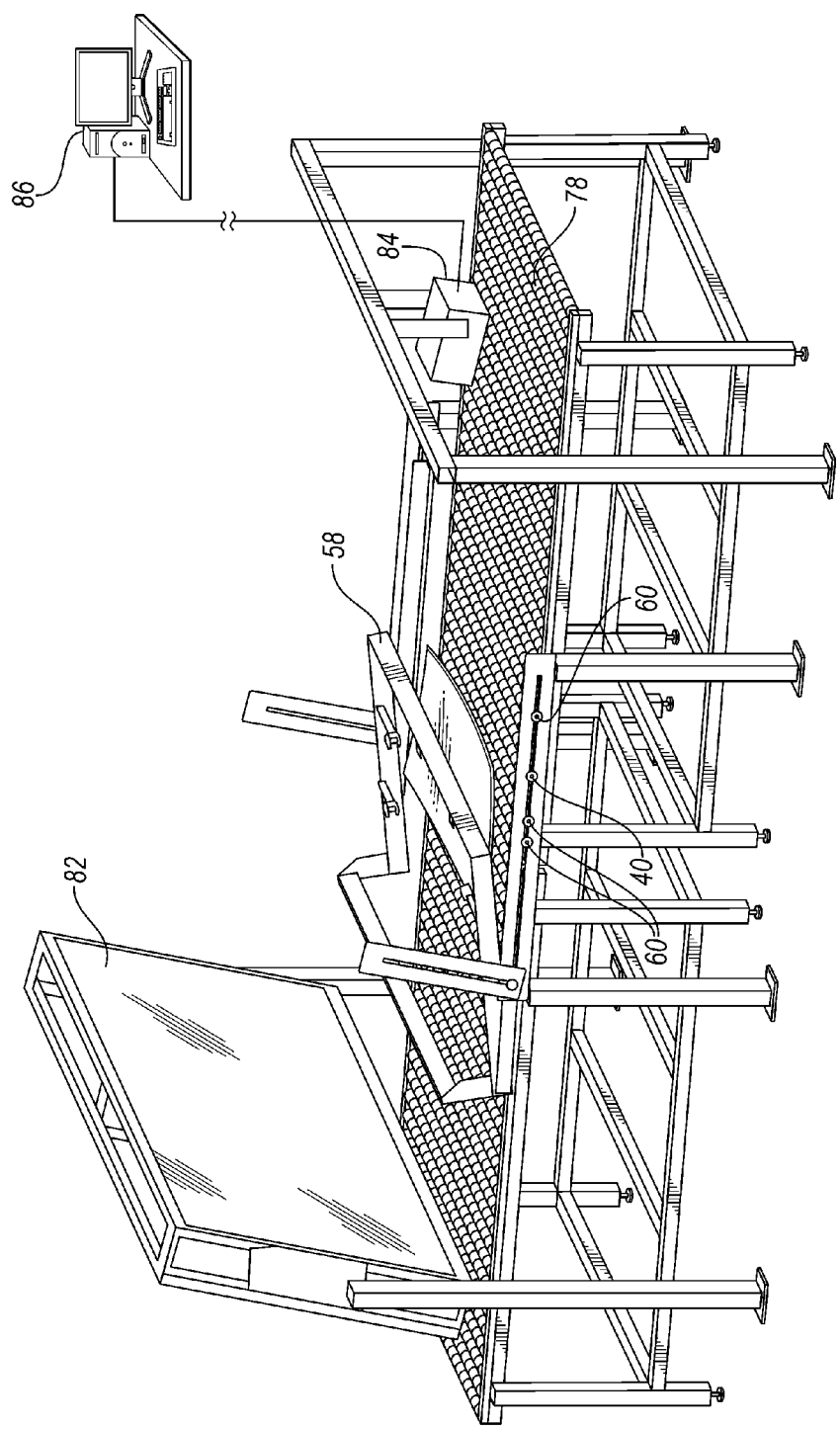
FIG. 3 is a perspective view of the disclosed glass sheet optical inspection system of FIG. 1 with the glass sheet acquisition and positioning mechanism positioned to release the glass sheet back onto the conveyor.

FIGS. 1-3 depict the glass sheet acquisition and positioning mechanism 10 in three functional positions, and best depict the associated method. In FIG. 1, mechanism 10 is oriented in a first position, generally parallel to and above the plane of the conveyor such that, as a glass sheet G travels downstream (i.e., from left to right in FIG. 1) the glass contacts locators 16 and is retained in position by mechanism 10. In FIG. 2, mechanism 10 is moved to a second position wherein the upstream end 56 of the mechanism and the glass sheet retained thereon is moved vertically upward to tilt mechanism 10 and the glass sheet to a preselected position. Camera 84 may then be activated by computer 86 to acquire an image of the screen 82 with the glass sheet interposed in the path of the camera 84 between the camera 84 and the screen 82 at the appropriate angle (e.g., the installation position of the glass sheet in a vehicle) to thereafter analyze the optical characteristics of glass sheet. In FIG. 3, mechanism 10 is moved to a third position wherein the downstream end 58 is tilted upward from the plane of the conveyor to thereby allow the glass sheet to be released from contact with the locators 16 for movement on the conveyor 78 to the next processing station.

As will be appreciated by those skilled in the art, vertical rails 26, 28 may be oriented such that, when support arms 34, 36 and the interior support frame 14 moved upwardly into the second position by slidably positioning upstream guides 38, 42 to the uppermost limit within guideways 30, 32, the upstream edge of the glass sheet is appropriately positioned between the camera and the screen. It will also be appreciated that downstream guide pins 40, 44 may be positioned at a suitable location along the length of support arms 34 and 36 such that, as mechanism 10 is moved to the second position, support arms 34 and 36 slide and pivot at guides 40, 44 within guideways 22 and 24 such that support arms 34 and 36 and the interior support frame (and the glass sheet retained therein) achieve the desired angle of orientation. It will be further appreciated that downstream guide 40, 44 may be located at various positions (indicated at 60 in the figures) to achieve the appropriate angle of orientation for the glass sheet during image acquisition. Each of pins 40, 44 may be releasably secured to support arms 34, 36 so that they may be moved to any of the alternative locations 60 as desired to adjust the angle of orientation as desired. Alternatively, a plurality of guide pins may be mounted on support arms 34, 36, each movable from an operable position wherein the guide pins are positioned within guideways 22, 24, to an inoperable position wherein the guide pins are not engaged within guideways 22 and 24, such that one of the plurality of guide pins on each support arm 34, 36 may be moved into its operable position to achieve the desired angle of orientation.

As best illustrated in FIG. 4, a plurality of interior support frames 14 may be provided, each with locators 16 positioned and moveable to accommodate different sizes and shapes of glass sheets, such that one interior support frame 14 may be quickly removed from the support arms 34, 36 and replaced with another interior support frame when, for example, a different glass sheet part design is being processed.

Referring again to FIGS. 1-3, an in-line glass sheet optical inspection system 80 is also disclosed. The in-line glass sheet optical inspection system 80 is mounted to inspect glass sheets as they are transported on a conveyor 78 associated with a glass sheet processing system which performs multiple fabricating operations on the glass sheets. The disclosed system 80 includes a background screen 82, a camera 84, and a glass sheet acquisition and positioning mechanism 10 for receiving a glass sheet as it is conveyed on one of the conveyors 78, momentarily removing the glass sheet from the conveyor and positioning the glass sheet in the path between the camera and the background screen so that the camera may capture an image of the screen pattern transmitted through the glass sheet, and then repositioning the glass sheet on the conveyor 78 for further processing. The inspection system 80 further includes a computer 86 including logic for receiving the captured image data and performing one or more optical processing operations to analyze the optical characteristics of the glass sheet and display or otherwise report selected information associated with the analysis. As previously described, computer 86 may also be operably connected to sensors mounted on the locators 16 and actuators mounted to move the interior support frame 14 to and from each of its three operating positions to controllably position glass sheets for image acquisition and optical processing as further described herein.

In one embodiment, the inspection system may be of the type described in U.S. Patent Application Publication No. 2012/0098959 A1, the disclosure of which Publication is hereby incorporated herein in its entirety. In this embodiment of the optical inspection system 80, the digital image acquired for each glass sheet is downloaded to the computer 86, which is suitably programmed to analyze the image data to determine (1) indicia, including the magnification and lens power, of optical distortion in the observed image of the pattern transmitted through the glass sheet, and (2) small visible optical or obstructive defects on the glass sheet.

In addition to the above-described optical distortion characteristics and data identified and displayed by the system 80, the disclosed system and method may also identify and locate areas of optical and/or obstructive distortion and other visible, defects as small as 1 millimeter in diameter, which appear on the glass sheet surface.

The system 80 may be programmed by the user to graphically and numerically display various indicia of optical distortion, including those indicia most relevant to industry standards such as ECE R43, or other indicia considered relevant in the industry to the analysis of the optical transmission quality of formed and fabricated glass sheets. The system 80 may, as well, be programmed to display the locations of small visible surface defects identified on the glass sheet.

In one embodiment, the background screen 82 provides pattern of dark squares positioned on a light background at a known predetermined distance from each other, forming a rectangular grid such that the image of the grid is projected onto the camera 84 through the glass sheet, G, mounted therebetween. It will be appreciated that other similar contrasting grid patterns may be employed without departing from the spirit of the present invention.

The digital camera 84 is mounted to collect images of the grid on screen 82 transmitted through the glass sheet G retained on the glass sheet acquisition and positioning mechanism 10. The camera 84 is connected via a conventional data line to a computer 86 which is suitably programmed to acquire the digital image data from the camera, process the image data to obtain the desired resolution for the data, and analyze the data to develop various indicia of distortion as well as small marks/defects on the surface of the glass sheet according to the method of the present invention as described herein, and as further described in U.S. Patent Application Publication No. 2012/0098959 A1. The computer 86 is also programmed to present the derived image distortion information in both graphical (e.g., color-coded images) and statistical forms. If desired, various other statistical data can be derived and reported for predefined areas of the glass sheet, including the maximum, minimum, range, mean, and standard deviation in lens power, or other indices of distortion which may be of interest.

As will be appreciated by those skilled in the art, in addition to the method and system described in U.S. Patent Application Publication No. 2012/0098959 A1, other embodiments of the optical inspection system 80 may additionally or alternatively employ other known image processing techniques to collect and analyze image data associated with the glass sheets and provide various indicia of transmitted optical distortion. Similarly, other methodologies for identifying marks and/or defects on the surface of the glass sheet may be developed and employed by the inspection system 80 without departing from the spirit of the present invention.

In one embodiment, the grid screen 82 is a light box that utilizes conventional lighting (such as fluorescent lights) behind a translucent panel upon which a contrasting pattern, preferably in the form of a black-square-on-white background grid, is printed, painted, or otherwise applied using conventional methods. The digital camera 84 is connected to the computer 86 using known methods, preferably so that the acquisition of the image by the camera may be controlled by the computer.

Figure 8:
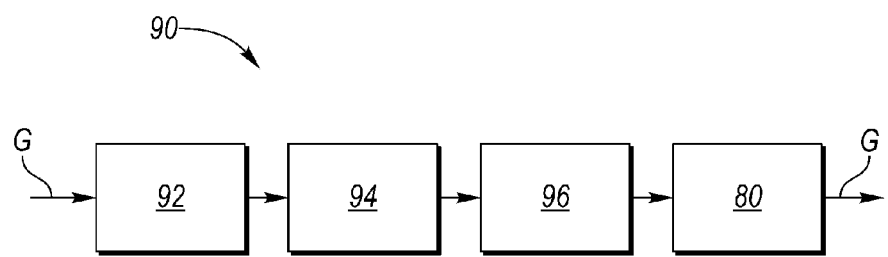
FIG. 8 is a schematic diagram of one embodiment of the disclosed in-line optical inspection system installed in a typical automotive backlite forming and tempering line.

FIG. 8 illustrates a typical automotive backlite heating, bending, and tempering system 90 which includes the in-line optical inspection system 80 of the present invention. In this installation, the glass sheets (indicated as G) enter a heating zone 92 where the glass is softened to a temperature suitable for forming the glass into the desired shape. The heated glass sheet is then conveyed to a bending station 94 where the softened sheet is formed to the desired shape, and thereafter further conveyed to a cooling station 96 where the glass sheet is cooled in a controlled manner to achieve the appropriate physical characteristics. In this embodiment, the glass sheet would then be conveyed out of the cooling station onto a conveyor from which the sheet is acquired and positioned by the acquisition and positioning mechanism 10 for image acquisition and analysis by the optical inspection system 80 according to the present invention. Following the measurement, the glass sheet would then be returned to the conveyor 78 for further processing. It will be appreciated that the transport and conveyance of the glass can be achieved by using known techniques such as by roller, air-float, or belt conveyors, positioners, and robotic arms, in order to handle the glass in the manner described.

Figure 9:
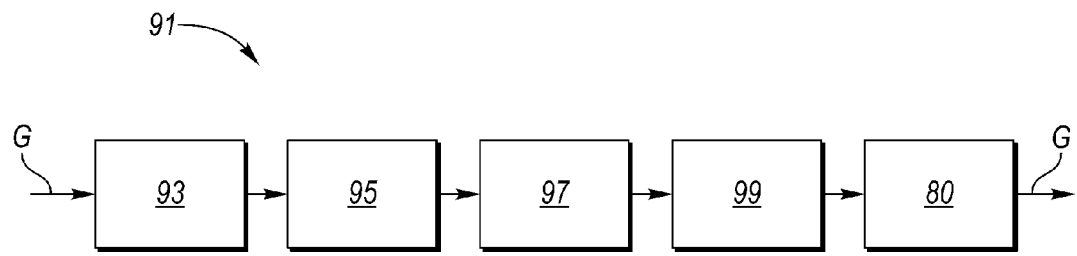
FIG. 9 is a schematic diagram of another embodiment of the disclosed in-line optical inspection system installed in a typical automotive windshield forming line.

FIG. 9 similarly schematically illustrates an in-line optical inspection system 80 of the present invention in a typical windshield fabrication system 91, which may include a heating station 93, a bending station 95, a cooling station 97, and a lamination station 99, upstream of the optical inspection system 80.

It will be appreciated that the optical inspection system 80 of the present invention could alternatively be mounted in-line at various other points in the above-described and other glass sheet fabrication systems as desired to maximize the production rate of the system, so long as the optical distortion measurements are taken after the glass sheet has been formed to its final shape.

It will also be appreciated by those skilled in the art that, although the camera and array screen are arranged in the illustrated embodiment such that the path between the camera 48 and background array 82 is parallel to the direction of conveyance of the glass, various alternative arrangements of the system 80 along the conveyor 78 may be employed without departing from the spirit of the invention.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A glass sheet acquisition and positioning mechanism for an inline system for measuring optical characteristics of a glass sheet, which inline system includes a background screen including contrasting elements arranged in a predefined pattern, a digital camera for acquiring an image of the background screen with the glass sheet positioned between the camera and the screen at a preselected position, and which inline system is installed in a system for fabricating glass sheets including one or more processing stations and one or more conveyors for conveying the glass sheet from station to station during processing, the acquisition and positioning mechanism comprising:

an exterior support frame mountable in proximity to one of the one or more conveyors between the camera and the background screen;

first and second support arms configured to be operably connected to the exterior support frame for slidable and pivotal movement with respect to the exterior support frame; and an interior support frame configured to be supported on the first and second support arms so that the interior support frame is selectively positionable with respect to the exterior support frame from a first generally horizontal orientation in a plane of the glass sheet on the one conveyor to a second, upwardly-tilted orientation whereby an upstream end of the interior support frame is elevated from a plane of the one conveyor with the glass sheet retained thereon to thereby position the glass sheet between the camera and the screen at the preselected position, and so that the interior support frame is thereafter positionable to a third orientation for releasing the glass sheet retained in the interior support frame for continued movement on the one conveyor.

2. The glass sheet acquisition and positioning mechanism of claim 1 further including one or more locators mountable in proximity to the one conveyor such that, when the interior support frame is positioned in its first orientation, the one or more locators are positioned or positionable to catch a glass sheet as it is moving on the one conveyor and retain the glass sheet in position for securing the glass sheet on the interior support frame.

3. The glass sheet acquisition and positioning mechanism of claim 2 wherein at least one of the one or more locators is mounted on the interior support frame.

4. The glass sheet acquisition and positioning mechanism of claim 2 wherein the one or more locators comprise a first location including an actuator which may be selectively operated to move the first locator into contact with the glass sheet to position and retain the glass sheet within the interior support frame.

5. The glass sheet acquisition and positioning mechanism of claim 4 wherein the actuator may be selectively operated to move the first locator out of contact with the glass sheet to facilitate release of the glass sheet from the interior support frame onto the one conveyor.

6. The glass sheet acquisition and positioning mechanism of claim 1 wherein the third orientation of the interior support frame is an upwardly-tilted orientation in which a downstream end of the interior support frame is upwardly tilted to facilitate release of a glass sheet retained in the interior support frame onto the one conveyor.

7. The glass sheet acquisition and positioning mechanism of claim 1 wherein, when the acquisition and positioning mechanism is used with the inline system and the system for fabricating glass sheets, the support arms and the interior support frame are movable together when the interior support frame moves from the first generally horizontal orientation to the second, upwardly-tilted orientation, and the interior support frame is movable with respect to the support arms when the interior support frame moves from the second, upwardly-tilted orientation to the third orientation.

8. A glass sheet acquisition and positioning mechanism for an inline system for measuring optical characteristics of a glass sheet, which inline system includes a background screen including contrasting elements arranged in a predefined pattern, a digital camera for acquiring an image of the background screen with the glass sheet positioned between the camera and the screen at a preselected position, and which inline system is installed in a system for fabricating glass sheets including a heating station for heating the glass sheet to a temperature adequate to soften the glass sheet for forming into a desired shape, a bending station for forming the softened glass sheet to the desired shape, a cooling station for cooling the formed glass sheet in a controlled manner, and one or more conveyors for conveying the glass sheet from station to station during processing, the acquisition and positioning mechanism comprising:

an exterior support frame mountable in proximity to one of the one or more conveyors between the camera and the background screen, the exterior support frame including first and second generally horizontal rails mountable, respectively, on opposite sides of the one conveyor, each of the generally horizontal rails having a guideway, and first and second generally vertical rails mountable, respectively, on opposite sides of the one conveyor, each of the generally vertical rails having a guideway;

first and second support arms, the first support arm including a first positioning guide configured to be operably connected for slidable and pivotal movement in the guideway of the first generally vertical rail and a second positioning guide configured to be operably connected for slidable and pivotal movement in the guideway of the first generally horizontal rail, the second support arm including a first positioning guide configured to be operably connected for slidable and pivotal movement in the guideway of the second generally vertical rail and a second positioning guide configured to be operably connected for slidable and pivotal movement in the guideway of the second generally horizontal rail;

an interior support frame including
  first and second elongate, generally parallel, spaced-apart side members,
  a cross-member extending transverse to and interconnecting the side members, thereby defining a generally u-shaped support that is open at an upstream end relative to a direction of conveyance of the one conveyor when the interior support frame is positioned in a first generally horizontal orientation in a plane of the glass sheet on the one conveyor, and
  one or more locators connected to one or more of the first side member, the second side member or the cross-member such that, when the interior support frame is positioned in its first orientation, the one or more locators are positioned to catch and retain the glass sheet as it is moving on the one conveyor, wherein
  each of the first and second side members includes an upstream support element positionable upstream relative to the direction of conveyance, which upstream support elements of the first and second side members are configured to be supported, respectively, by the first and second support arms, and each of the first and second side members includes a downstream support element positionable downstream in the direction of conveyance, which downstream support elements of the first and second side members are configured to be releasably supported, respectively, by the first and second support arms, such that the first and second support arms may be slidably and pivotally positioned to move the interior support frame from the first generally horizontal orientation to a second, upwardly tilted orientation whereby the open end of the interior support frame is elevated from a plane of the conveyor;

a first actuating mechanism including at least one actuator configured to contact at least one of the support arms to move the support arms at locations of the first positioning guides along the guideways of the first and second generally vertical rails to thereby move the interior support frame from the first orientation to the second orientation, thereby positioning a glass sheet retained by the interior support frame in a selected orientation between the camera and the background screen; and a second actuating mechanism including at least one actuator configured to contact the interior support frame and move the interior support frame, at locations of the downstream support elements, from the first orientation to a third, upwardly-tilted orientation in which an end of the interior support frame downstream in the direction of conveyance is upwardly tilted to facilitate release of a glass sheet retained in the interior support frame for continued movement on the conveyor.

9. The glass sheet acquisition and positioning mechanism of claim 8 further including one or more locators mountable in proximity to the one conveyor such that, when the interior support frame is positioned in its first orientation, the one or more locators are positionable to catch a glass sheet as it is moving on the one conveyor and retain the glass sheet in position for acquisition of the glass sheet on the interior support frame.

10. The glass sheet acquisition and positioning mechanism of claim 9 wherein the one or more locators comprise a first locator including an actuator which may be selectively operated to move the first locator into contact with the glass sheet to position or retain the glass sheet within the interior support frame.

11. The glass sheet acquisition and positioning mechanism of claim 10 wherein the actuator may be selectively operated to move the first locator out of contact with the glass sheet to facilitate release of the glass sheet from the interior support frame.

12. The glass sheet acquisition and positioning mechanism of claim 8 wherein, when the acquisition and positioning mechanism is used with the inline system and the system for fabricating glass sheets, the support arms and the interior support frame are movable together when the interior support frame moves from the first orientation to the second orientation, and the interior support frame is movable with respect to the support arms when the interior support frame moves from the first orientation to the third orientation.

13. A system for fabricating glass sheets, the system comprising:
one or more processing stations;
one or more conveyors for conveying a glass sheet from station to station during processing; and
an inline apparatus for measuring optical characteristics of the glass sheet, the inline apparatus including:
a background screen including contrasting elements arranged in a pre-defined pattern;
a digital camera for acquiring an image of the background screen;
a glass sheet acquisition and positioning mechanism for receiving the glass sheet as it is conveyed on one of the one or more conveyors, momentarily removing the glass sheet from the one conveyor, and positioning the glass sheet in a path between the camera and the background screen so that the camera may capture an image of the pattern transmitted through the glass sheet, the acquisition and positioning mechanism including:
an exterior support frame mounted in proximity to the one conveyor between the camera and the background screen;
first and second support arms operably connected to the exterior support frame for slidable and pivotal movement with respect to the exterior support frame; and
an interior support frame supported on the first and second support arms so that the interior support frame is selectively positionable with respect to the exterior support frame from a first generally horizontal orientation in a plane of the glass sheet on the one conveyor to a second, upwardly-tilted orientation in which an upstream end of the interior support frame is elevated from a plane of the one conveyor with the glass sheet retained thereon to thereby position the glass sheet between the camera and the screen at the preselected position, and so that the interior frame is thereafter positionable to a third orientation for releasing the glass sheet retained in the interior support frame for continued movement on the one conveyor; and
a computer including logic for receiving the captured image data associated with the glass sheet and performing one or more processing operations using the captured image data to analyze the optical characteristics of the glass sheet.

14. The sheet system of claim 13 wherein the acquisition and positioning mechanism further includes one or more locators mounted in proximity to the one conveyor such that, when the interior support frame is positioned in its first orientation, the locators are positioned or positionable to catch a glass sheet as it is moving on the one conveyor and retain the glass sheet in position for securing the glass sheet on the interior support frame.

15. The system of claim 14 wherein at least one of the one or more locators is mounted on the interior support frame.

16. The system of claim 14 wherein the one or more locators comprise a first locator including an actuator which may be selectively operated to move the first locator into contact with the glass sheet to position and retain the glass sheet within the interior support frame.

17. The system of claim 16 wherein the actuator may be selectively operated to move the first locator out of contact with the glass sheet to facilitate release of the glass sheet from the interior support frame onto the one conveyor.

18. The system of claim 13 wherein the third orientation of the interior support frame is an upwardly-tilted orientation in which a downstream end of the interior support frame is upwardly tilted to facilitate release of a glass sheet retained in the interior support frame onto the one conveyor.

19. The system of claim 13 wherein the interior support frame is releasably supported on the support arms so that the support arms and the interior support frame are movable together when the interior support frame moves from the first generally horizontal orientation to the second, upwardly-tilted orientation, and so that the interior support frame is movable with respect to the support arms when the interior support frame moves to the third orientation.

20. A system for fabricating glass sheets, the system comprising:
a heating station for heating the glass sheet to a temperature adequate to soften the glass for forming into a desired shape;
a bending station for forming the softened sheet to the desired shape;
a cooling station for cooling the formed glass sheet in a controlled manner;
one or more conveyors for conveying the glass sheet from station to station during processing; and an inline apparatus for measuring optical characteristics of the glass sheet, the inline apparatus including:
  a background screen including contrasting elements arranged in a pre-defined pattern,
  a digital camera for acquiring an image of the background screen,
  a glass sheet acquisition and positioning mechanism for receiving a glass sheet as it is conveyed on one of the one or more conveyors, and momentarily removing the glass sheet from the one conveyor and positioning the glass sheet in a path between the camera and the background screen so that the camera may capture an image of the pattern transmitted through the glass sheet, the acquisition and positioning mechanism including:
    an exterior support frame mounted in proximity to the one conveyor between the camera and the background screen, the exterior support frame including first and second generally horizontal rails mounted, respectively, on opposite sides of the one conveyor, each of the horizontal rails having a guideway, and first and second generally vertical rails mounted, respectively, on opposite sides of the one conveyor, each of the vertical rails having a guideway;
    first and second support arms, the first support arm including a first positioning guide operably connected for slidable and pivotal movement in the guideway of the first generally vertical rail and a second positioning guide operably connected for slidable and pivotal movement in the guideway of the first generally horizontal rail, the second support arm including a first positioning guide operably connected for slidable and pivotal movement in the guideway of the second generally vertical rail and a second positioning guide secured to the support arm and operably connected for slidable and pivotal movement in the guideway of the second generally horizontal rail;
    an interior support frame including
      first and second elongate, generally parallel, spaced-apart side members,
      a cross-member extending transverse to and interconnecting the side members, thereby defining a generally u-shaped support having an open end that faces upstream relative to a direction of conveyance of the one-conveyor when the interior support frame is positioned in a first generally horizontal orientation in a plane of the glass sheet on the one conveyor,
      one or more locators connected to one or more of the first side member, the second side member or the cross-member such that, when the interior support frame is positioned in its first orientation, the locators are positioned to catch and retain a glass sheet as it is moving on the one conveyor,
      wherein each of the first and second side members includes an upstream support element which is supported by a respective one of the first and second support arms, and each of the first and second side members includes a downstream support element which is releasably supported by a respective one of the first and second support arms, such that the first and second support arms may be slidably and pivotally positioned to move the interior support frame from the first generally horizontal orientation to a second upwardly-tilted orientation whereby the open end of the interior support frame is elevated from the plane of the one conveyor;
    a first actuating mechanism including at least one actuator associated with at least one of the first and second support arms to contact the at least one support arm and move the support arms at locations of the first positioning guides along the guideways of the first and second generally vertical rails to move the interior support frame from the first orientation to the second orientation, thereby positioning a glass sheet retained by the interior support frame in a selected orientation between the camera and the background screen; and
    a second actuating mechanism including at least one actuator associated with the interior support frame to contact the interior support frame and move the interior support frame at locations of the downstream support elements from the first orientation to a third, upwardly tilted orientation in which a closed end of the interior support frame is upwardly tilted, thereby releasing a glass sheet retained in the interior support frame for continued movement on the one conveyor; and
    a computer including logic configured to receive the captured image data associated with a selected glass sheet and perform one or more processing operations using the captured image data to analyze the optical characteristics of the glass sheet.

21. The system of claim 20 further including one or more locators mounted in proximity to the one conveyor such that, when the interior support frame is positioned in its first orientation, the one or more locators are positioned to catch a glass sheet as it is moving on the one conveyor and retain the glass sheet in position for acquisition of the glass sheet on the interior support frame.

22. The system of claim 21 wherein the one or more locators comprise a first locator including an actuator which may be selectively operated to move the first locator into contact with the glass sheet to position or retain the glass sheet within the interior support frame.

23. The system of claim 22 wherein the actuator may be selectively operated to move the first locator out of contact with the glass sheet to facilitate release of the glass sheet from the interior support frame.

24. The system of claim 20 wherein the support arms and the interior support frame are movable together when the interior support frame moves from the first orientation to the second orientation, and the interior support frame is movable with respect to the support arms when the interior support frame moves from the first orientation to the third orientation.

25. A method for acquiring and positioning a glass sheet in an inline system for measuring optical characteristics of the glass sheet, which inline system includes a background screen including contrasting elements arranged in a pre-defined pattern, a digital camera for acquiring an image of the background screen with the glass sheet positioned between the camera and the screen at a preselected position, and which inline system is installed in a system for fabricating glass sheets including one or more processing stations and a conveyor arrangement including one or more conveyors for conveying the glass sheet from station to station during processing, the method comprising:

providing an exterior support frame mounted in proximity to the conveyor arrangement between the camera and the background screen;
providing an interior support frame operably connected to the exterior support frame using first and second support arms for movement of the interior frame to a plurality of positions, wherein the first and second support arms are operably connected to the exterior support frame for slidable and pivotal movement with respect to the exterior support frame, and the interior support frame is supported on the first and second support arms;
positioning the interior support frame in a first generally horizontal orientation in a plane of the glass sheet on the conveyor arrangement;
capturing and retaining a glass sheet in the interior support frame as it is transported on the conveyor arrangement;
positioning the interior support frame in a second, upwardly-tilted orientation whereby an upstream end of the interior support frame is elevated from a plane of the conveyor arrangement with the glass sheet retained thereon to thereby position the glass sheet between the camera and the screen at the preselected position;
positioning the interior support frame in a third orientation; and
releasing the glass sheet retained in the interior support frame for continued movement of the glass sheet on the conveyor arrangement.

26. The method of claim 25 wherein the step of positioning the interior support frame in a third orientation includes positioning the interior support frame in an upwardly-tilted orientation in which a downstream end of the interior support frame is upwardly tilted.

* * * * *

UNITED STATES PATENT AND TRADEMARK OFFICE
CERTIFICATE OF CORRECTION

PATENT NO. : 9,933,373 B2  
APPLICATION NO. : 14/264231  
DATED : April 3, 2018  
INVENTOR(S) : Michael Vild et al.

Page 1 of 1

It is certified that error appears in the above-identified patent and that said Letters Patent is hereby corrected as shown below:

In the Claims

Column 12, Line 25, Claim 14:
After "The"
Delete "sheet".

Signed and Sealed this
Nineteenth Day of May, 2020

Andrei Iancu
*Director of the United States Patent and Trademark Office*